United States Patent [19]

Mark, deceased et al.

[11] Patent Number: 4,749,799

[45] Date of Patent: Jun. 7, 1988

[54] PREPARATION OF CHROMANS

[75] Inventors: Victor Mark, deceased, late of Evansville, Ind.; Esther H. Mark, legal representative, Springville, N.Y.; Carol M. Mark, legal representative, Evansville, Ind.

[73] Assignee: General Electric Company, Mt. Vernon, Ind.

[21] Appl. No.: 869,232

[22] Filed: Jun. 2, 1986

[51] Int. Cl.$^4$ .................................... C07D 311/04
[52] U.S. Cl. ................................................ 549/406
[58] Field of Search ...................................... 549/406

[56] References Cited

U.S. PATENT DOCUMENTS 3,359,281 12/1967 Schlichting et al. ............... 549/406
3,825,562 7/1974 Jaquiss ................................ 549/406

*Primary Examiner*—Nicky Chan
*Attorney, Agent, or Firm*—Joseph T. Eisele; Martin B. Barancik

[57] ABSTRACT

Chromans such as Chroman-I are prepared by the reaction of a corresponding phenol with diacetone alcohol.

6 Claims, No Drawings

PREPARATION OF CHROMANS

BACKGROUND OF THE INVENTION

1. Field of the Invention

The invention relates to a method of preparing chromans and more particularly relates to the method of preparing chromans by the reaction of diacetone alcohol with a phenolic compound.

2. Brief Description of the Prior Art

Chroman-I, i.e.; p-[2,2,4-trimethyl-4-(4-hydroxyphenyl)chroman] is a well known compound useful to terminate polycarbonate resins; see for example U.S. Pat. No. 3,697,481. It was first obtained by Dianin in 1914, from the reaction of phenol, mesityl oxide and hydrogen chloride, by a slow process (4 weeks). A flavan structure was incorrectly assigned; A. P. Dianin, J. Russian Physical Chemical Society, 46, 1310 (1914). The correct structure was determined by Baker, et al., via degradation; they also reduced reaction time to 4 days, and obtained a 36% yield (W. Baker, et al., J. Chem. Soc., 1965, 2010). The structure was confirmed by rational synthesis (W. Baker, et al., ibid, 1956, 2018). More recently, the compound was obtained by isolation from bisphenol-A streams by its adduction with ethanol; see Netherlands Patent Application, No. 6,515,583.

The method of the present invention employs relatively inexpensive reactants and results in commercially important yields with favorable economic advantages.

SUMMARY OF THE INVENTION

The invention comprises a method for the preparation of chromans of the formula:

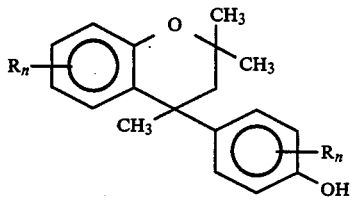

(I)

wherein each R is independently selected from the group consisting of hydrogen, halogen and lower alkyl and n is a whole number integer of from 0 to 2, which comprises;

reacting 4-hydroxy-4-methyl-2-pentanone with a stoichiometric proportion of a phenol selected from those of the formula:

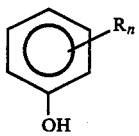

(II)

wherein R and n are as defined above, provided that at least one ring position ortho to the hydroxyl group is unsubstituted.

The term "lower alkyl" as used herein means the monovalent moiety obtained by removal of a hydrogen atom from a parent hydrocarbon, said hydrocarbon having from 1 to 5 carbon atoms, inclusive. Representative of lower alkyl are methyl, ethyl, propyl, isopropyl, butyl, isobutyl, tertiary butyl, pentyl, neopentyl, and the like.

The term "halogen" is used herein to mean chlorine, bromine, iodine and fluorine. Preferably, halogen herein means chlorine and bromine.

DETAILED DESCRIPTION OF THE PREFERRED EMBODIMENTS OF THE INVENTION

The method of the invention may be carried out by bringing together stoichiometric proportions of the reactants in a suitable reaction vessel. The reactants are all well known compounds as are methods of their preparation. Representative of the phenolic compounds of the formula (II) given above are phenol, m-cresol, p-cresol, p-ethylphenol, p-n-propylphenol, p-t-butylphenol, p-n-amylphenol, p-t-amylphenol, 3,5-dimethylphenol, m-chlorophenol, p-chlorophenol, sym-m-dichlorophenol and the like.

Rather than utilizing only one phenol reactant a mixture of two different phenol reactants may be employed.

The reactants are brought together in stoichiometric proportions to produce the chromans of formula (I), i.e.; one mole of the ketone is reacted with two moles of the phenol of formula (II). Generally, the phenol (II) reactant is present in the reaction mixture in a molar excess. The reaction proceeds smoothly, advantageously in the presence of an acid catalyst.

Some illustrative, non-limiting examples of acid catalysts that may be employed include hydrochloric acid, hydrobromic acid, poly(styrene sulfonic acid), sulfuric acid, benzene sulfonic acid, toluene sulfonic acid, and the like.

In another embodiment of the invention, we have found that insoluble polymers, which may be organic or inorganic in nature, and having pendant sulfonic acid groups are effective catalysts for promoting the method of the invention. Representative of such catalysts are the sulfonated styrene-divinylbenzene copolymers represented by recurring units of the general formula:

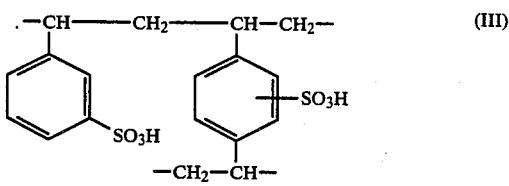

(III)

Such copolymers are well known as is the method of their preparation. They are also commercially available under the tradenames Amberlite and Amberlyst (Rohn and Hass, Philadelphia, Pa.). Preferably they are employed in their macroreticular resin forms. Preferred catalysts are also represented by those selected from polymeric fluorocarbons containing a repeating or recurring group selected from the formulae consisting of:

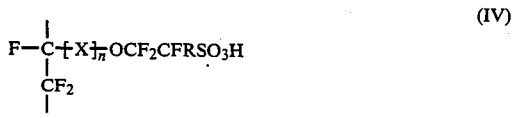

(IV)

-continued $$F-\overset{|}{\underset{|}{C}}-[X]_{\overline{n}}OCF_2CFRSO_3H \quad (V)$$
$$\underset{|}{CF_2} \quad SO_3H$$

and $$\overset{O}{\underset{||}{-C}}-CF_2-SO_3H \quad (VI)$$

wherein n is 0, 1 or 2; R is selected from fluorine and perfluoroalkyl radicals having from 1 to 10 carbon atoms; and X is selected from the group consisting of:

[O(CF$_2$)$_m$], [OCF$_2$CFY] and [OCFYCH$_2$]

wherein m is an integer of from 2 to 10 and Y is selected from the class consisting of fluorine and trifluoromethyl.

In a preferred embodiment, n is 1 or 2, Y is a trifluoromethyl radical, R is fluorine, and m is 2. Catalysts of the above formulae (IV), (V) and (VI) typically have a molecular weight of between about 1,000 and 500,000.

Polymeric catalysts within the above formulae (IV), (V) and (VI) may be prepared in various ways. One method, disclosed in U.S. Pat. No. 3,282,875 and in U.S. Pat. No. 3,882,093, comprises polymerizing vinyl compounds of the formula:

$$CF_2=CF[X]_nOCF_2CFRSO_2F \quad (VII)$$

or $$CF_2=CF[X]_nOCFSO_2FCF_2-R \quad (VIII)$$

wherein R, X and n have the meanings given to them above, in a perfluorocarbon solvent using a perfluorinated free radical initiator. The products are homopolymers of the compounds (VII) or (VIII) with repeating moieties of formula (IV) or (V) or copolymers of both with recurring moieties of the same formulae (IV) and (V). Since the vinyl ethers (VII) and (VIII) are liquid at reaction conditions, it is further possible to polymerize and copolymerize them in bulk without the use of a solvent. Polymerization temperatures vary from −50° C. to +200° C. depending on the initiator used. Pressure is not critical and is generally employed to control the ratio of the gaseous comonomer to the fluorocarbon vinyl ether. Suitable fluorocarbon solvents are known in the art and are generally perfluoroalkanes or perfluorocycloalkanes, such as perfluoroheptane or perfluorodimethylcyclobutane. Similarly, perfluorinated initiators are known in the art and include perfluoroperoxides and nitrogen fluorides. It is also possible to polymerize the vinyl ethers of formula (VII) or (VIII) in an aqueous medium using a peroxide or a redox initiator. The polymerization methods employed correspond to those established in the art for the polymerization of tetrafluoroethylene in aqueous media. The sulfonyl groups on the polymer may then be converted to sulfonic acid groups by known methods such as by contact with anhydrous or hydrous ammonia.

It is also possible to prepare catalysts for the present invention from the product of copolymerizing the vinyl ethers of formula (VII) or (VIII) with perfluoroethylene and/or perfluoroalpha-olefins. A preferred copolymer is prepared by polymerizing perfluoroethylene (tetrafluoroethylene) with a perfluorovinyl ether containing attached sulfonyl acid groups such as perfluoro-3,6-dioxa-4-methyl-7-octensulfonic acid, followed by conversion to the corresponding sulfonic acid which would have recurring groups of the formula:

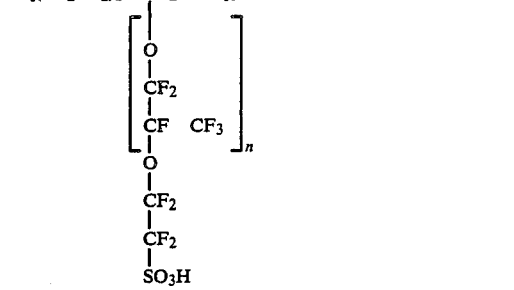

(IX)

wherein a is an integer of from 5 to 13.5, inclusive, b is such that the polymer of formula (IX) has a molecular weight of circa 1000; n is as defined above and the ratio of a over b varies from about 2 to about 50. The polymer of formula (IX) is available commercially under the tradename of NAFION ® resin (E. I. DuPont De Nemours and Company, Wilmington, Del.; see bulletin Z-189 dated 6/30/1978). Catalysts of the above-noted formula (IX) offer the advantages of high concentrations of accessible acid groups in a solid phase.

Another class of catalyst for use in the method of the invention comprises copolymers of the compounds of formulae (VII) and (VIII) given above with a silane monomer such as triethoxyvinyl silane and the like. The copolymerization may be carried out as described above, according to the schematic formulae:

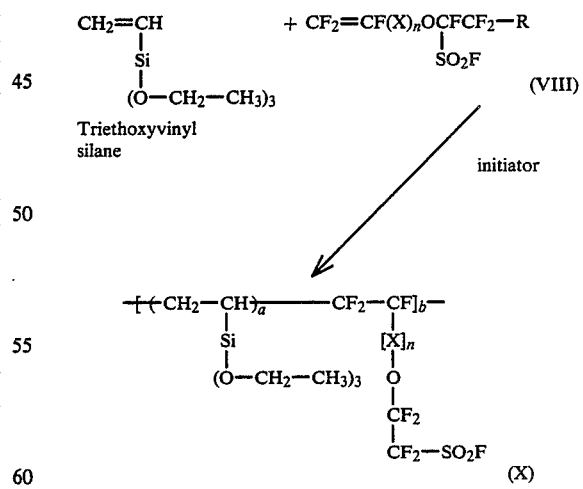

wherein a, n, b and X have the meaning previously ascribed to them, and the compound of formula (VIII) is used as representative of the compounds (VII) and (VIII). The product polymer of formula (X) may be further reacted with silica to remove ethanol and to give a perfluorinated sulfonic acid of the formula:

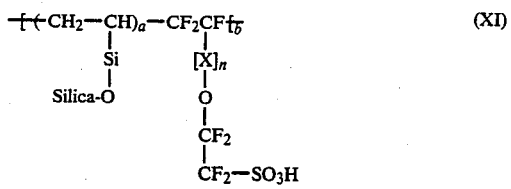

(XI)

wherein a, n, x and b are as defined above.

Another example of an insoluble catalyst useful in the method of the invention is one wherein a perfluoroorganosulfonyl fluoride is attached to an organic polymer containing reactive aromatic groups. Such an attachment may be represented by the schematic formulae:

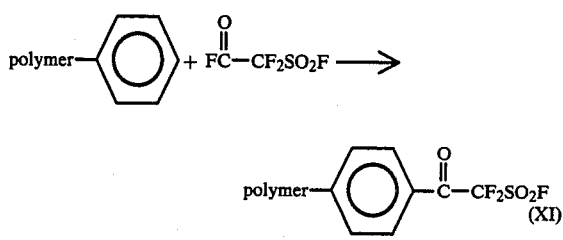

The reaction is carried out in the presence of anhydrous antimony pentafluoride or boron trifluoride. Acid hydrolysis of the product sulfonyl fluoride of formula (XI) will then give the corresponding polymer bound perfluorosulfonic acid group.

The insoluble catalyst employed in the present invention is advantageously a solid under reaction conditions. The catalyst broadly comprises a perfluorinated polymer having acid groups in the amount of about 0.01 to 5 mequiv/gram catalyst. Preferably, the polymer contains about 0.05 to 2 mequiv/gram of acid groups.

Advantageously the catalyst is used in a dried form, i.e.; substantially free of water.

The insoluble catalyst used in the present invention may be supported on a porous, solid inert support. The supported catalysts possess greater activity per unit of acid present than do the unsupported catalysts. By porous solid support is meant an inert support material having a porous structure and an average pore diameter of between about 50 Å and about 600 Å or higher. Preferably, the average pore diameter of the support is greater than about 200 Å. The porous solid support of the subject invention is preferably selected from the inorganic oxide group consisting of alumina, fluorided alumina, zirconia, silica, silica-alumina, magnesia, chromia, boria, and mixtures and combinations thereof. Other porous, solid supports may also also be used such as bauxite, kieselguhr, kaolin, bentonite, diatomaceous earth and the like. Other porous solid supports such as polytetrafluoroethylene, carbon, e.g., charcoal, polytrichlorofluoroethylene, porous glass, and the like may also be used. Basically, the support should be substantially inert to the catalyst, and be insoluble in the reaction mixture under reaction conditions.

The average pore diameter (also known as effective pore diameter) of the support, which is related to the ratio of pore volume to surface area, is an important consideration in the choice of support. Generally, as the average pore diameter of the support is increased, the activity of the catalyst is increased. Most preferably, the support should possess both a high surface area and a high average pore diameter.

The weight ratio of catalyst to support may vary from about 0.1:100 to about 30:100, preferably from about 1:100 to about 15:100. The support is preferably impregnated with the catalyst by dissolving the catalyst in a solvent, such as ethanol, mixing the support and the catalyst solution, and then drying the impregnated support under vacuum at a temperature of between about 25° C. and about 100° C. so as to remove the solvent.

The amount of the acid catalysts employed is a catalytic amount. By catalytic amount is meant an amount effective to catalyze the reaction between the ketone and the phenol (II) to produce the compound of formula (I). Generally, this amount is in the range of from about 0.1 to about 10 percent by weight of the reactants. However, it may be somewhat higher since the water coproduct formed in the reaction dilutes the acid catalyst and may render it somewhat less effective (slowing the reaction) than in its undiluted state.

Cocatalysts such as butyl mercaptan may also be used in the process of the invention.

The phenol of Formula (II) is reacted with the ketone under conditions of temperature and pressure, and in the presence of the acid catalyst, such that coreaction between said phenol and said ketone will occur to form the chroman of formula (I). The reaction proceeds satisfactorily under about one atmosphere of pressure and at temperatures of from about room temperature (25° C.) to about 100° C. Higher or lower temperatures and pressures may be employed but are generally not necessary. The reaction is exothermic and the desired temperature range may be maintained by the controlled addition of acid catalyst to the reaction mixture or by cooling the reaction mixture.

The reaction may also be carried out in the presence of a solvent for the reactants. Representative of such solvents are methylene chloride, alcohols such as methanol and the like.

Completion of the reaction may be observed by cessation of an exotherm in the reaction mixture. Upon completion of the reaction, the desired product of formula (I) may be separated from the reaction mixture by conventional means, such as by neutralization of catalyst, distillation of catalyst, solvent and excess phenol reactant, filtration of solids, and like techniques.

The process and method of the invention may be carried out either as a batch or continuous type of operation.

When employing a continuous process, the feedstocks may be contacted with an insoluble catalyst such as described above, in any suitable reactor. In one embodiment, the catalyst is packed in a vertical, tubular reactor bed with inert supports, such as ceramic balls or silicon carbide, above and below the catalyst to prevent entrainment of the solid catalyst. In a further embodiment, the catalyst is mixed with an inert material, such as quartz, and loaded in the reactor so as to improve the fluid dynamics of the system. The flow of the reactant feed stream may be upflow or downflow, with an upflow arrangement being preferred to ensure a liquid phase reaction. Alternatively, the catalyst particles may be used in a fluidized bed or the catalyst may be formed into a tube or membrane.

The following preparations and examples describe the manner and process of making and using the invention and set forth the best mode contemplated by the inventor for carrying out the invention but are not to be construed as limiting the scope of the invention.

PREPARATION 1

An appropriate vessel is charged with a quantity of Nafion® XR resin (K⊕ form; E. I. DuPont De Nemours, Wilmington, Del.) particles and an equal weight of 4N hydrochrloric acid. The charge is stirred at room temperature for 4 hours. At the end of this period the resin is separated by filtration and washed with water. The above precedure is repeated 4 additional times to obtain more than 95 percent conversion of the resin to the H⊕ form. The resin is then washed with water and dried in a vacuum oven at a temperature of 80°–90° C. The resin catalyst contains about 0.83 meg. of acid per gram of catalyst.

The structure for the resulting catalyst is exemplified by the formula (IX) given above wherein n is 1.

PREPARATION 2

A polymeric perfluorotriethoxysilane is prepared as follows:

A stainless steel autoclave is charged with deionized water, di-tertiary-butylperoxide and perfluoro-3,5-dioxa-4-methyl-7-octensulfonic acid in equal weight proportions. The autoclave is sealed, evacuated, and then charged with vinyltriethoxysilane by transfer in vacuo. The autoclave is placed in an electrical heating jacket and held at 123°–125° C. for 18.5 hours. Maximum pressure is reached after the first 2 hours of heating and the pressure decreases as the polymerization proceeds.

After the reaction period, the autoclave is cooled, vented, and opened. The contents consist of precipitated copolymer suspended in a liquid phase. The copolymer is vacuum filtered, washed with ethanol, and then distilled water. It is dried in a vacuum oven at 60° C.

The dried copolymer is then mixed with silica having an average pore diameter of between 50 Å and about 600 Å and the resultant intimate mixture is heated until 3 moles of ethanol per mole of copolymer are collected. The resultant material consists of a perfluorinated sulfonic acid moiety bound to silica and having a formula within the scope of the formula (XI) given above.

PREPARATION 3

A series of resins (styrene-divinyl benzene resins which contain 1 to 12% divinylbenzene) are swollen in a toluene solution at 100° under nitrogen in a 450 ml Parr reactor. These swollen resins are then acylated with

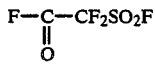

in the presence of anhydrous antimony pentafluoride or boron trifluoride. The reaction is conducted in a 450 ml Parr reactor at 100° for 24 hours. The solvent is decanted, and the polymer beads are extracted (Soxhlet) for 24 hours with benzene under nitrogen to remove unreacted unbound catalyst from the resin. The total amount of catalyst bound is determined in the usual way after conversion to the acid form. By controlling the degree of swelling of the resins, a size selectivity could be conferred on the catalyst system by the polymer. The same type reaction is carried out with sulfonyl fluoride adducts.

EXAMPLE 1

A suitable reaction vessel is charged with 188 g (2 moles) of melted phenol and 23.2 g (0.2 moles) of 4-hydroxy-4-methyl-2-pentanone (diacetone alcohol). The charge is cooled while stirring to a temperature of circa 35° C. and hydrochloric acid added dropwise. With continued stirring, the temperature of the reaction mixture is maintained within the range of from about 25° C. to about 35° C. After about 1 hour, the reaction is complete. The reaction mixture is allowed to cool to room temperature and filtered to remove solid crystals of p-[2,2,4-trimethyl-4-(4-hydroxyphenyl)chroman]. The product is recrystallized from benzene.

EXAMPLE 2

A reactor is constructed so as to have a stainless steel coil which contains a section of NAFION-H (DuPont, supra.) tubing of 2.75 MM ID and 3.125 MM OD and approximately 6 feet in length (9.75 gm). The Nafion-H has an equivalent weight of 1100. This tubing is immersed in an ice bath equipped with a temperature controller and stirrer. The bath is used to maintain the reaction mixture at a temperature of 25° C. to 35° C. A mixture of phenol and diacetone alcohol (10:1 molar ratio) is passed through the NAFION tube. A flow rate of 3.7 ml min$^{-1}$ is employed. The product is passed through an in-line filter prior to collection. Analysis shows the solid product exiting from the reactor to be Chroman-I.

EXAMPLE 3

A column is packed with two grams of NAFION-H powder (DuPont, supra.) resting on approximately 2 cm of glass wool. The column is cooled so that the temperature of the NAFION-H is 25° C.–35° C. during reaction. A solution of phenol and diacetone alcohol (10:1 molar ratio) is then added at such a rate that it has a residence time in the NAFION-H section of the column, of approximately 15 minutes. Analysis of the effluent from the reaction shows it to contain crystals of Chroman-I.

EXAMPLE 4

A solution of phenol and diacetone alcohol (10:1 molar ratio) is passed over a catalyst prepared as described in Preparation 2, supra., at a rate so as to have a residence time of between 10–15 minutes in the catalyst section of the reactor which is maintained at 25° C.–35° C. Analysis of the effluent from the reactor shows it to contain crystals of Chroman-I.

EXAMPLE 5

A solution of phenol and diacetone alcohol (10:1 molar ratio) is stirred at 25° C. with a catalyst prepared as described in Preparation 3, supra. After a period of 3 hours, the polymer bound perfluororganosulfonic acid catalyst is removed via filtration. Analysis of the residue crystals show it to be Chroman-I.

It is claimed is:

1. A method for the preparation of chromans of the formula:

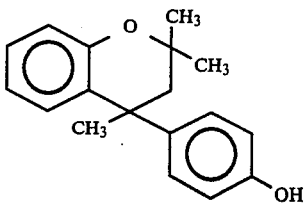

which comprises;
reacting 4-hydroxy-4-methyl-2-pentanone with a stoichiometric proportion of phenol.

2. The method of claim 1 wherein the phenol is present in a molar excess.

3. The method of claim 1 wherein a catalyst is present and is within the range of from about 0.1 to 10 percent by weight of the reactants.

4. The method of claim 1 carried out at a temperature within the range of from room temperature to 100° C.

5. The method of claim 1 wherein a catalyst is present and is insoluble in the reaction mixture.

6. The method of claim 5 wherein the insoluble catalyst comprises a polymer having pendant organosulfonic acid groups.

* * * * *